US012637404B2

(12) United States Patent
Benton

(10) Patent No.: US 12,637,404 B2
(45) Date of Patent: May 26, 2026

(54) METHODS AND SYSTEMS FOR CONCENTRATING ACETIC ACID SOLUTIONS WITH A MULTI-TIER, ULTRAHIGH PRESSURE REVERSE OSMOSIS

(71) Applicant: PORIFERA, INC., San Leandro, CA (US)

(72) Inventor: Charles Knight Benton, Berkley, CA (US)

(73) Assignee: Porifera, Inc., San Leandro, CA (US)

( * ) Notice: Subject to any disclaimer, the term of this patent is extended or adjusted under 35 U.S.C. 154(b) by 555 days.

(21) Appl. No.: 18/245,356

(22) PCT Filed: Sep. 14, 2021

(86) PCT No.: PCT/US2021/050330
§ 371 (c)(1),
(2) Date: Mar. 15, 2023

(87) PCT Pub. No.: WO2022/060747
PCT Pub. Date: Mar. 24, 2022

(65) Prior Publication Data
US 2023/0372868 A1 Nov. 23, 2023

Related U.S. Application Data

(60) Provisional application No. 63/078,518, filed on Sep. 15, 2020.

(51) Int. Cl.
| | |
|---|---|
| *C07C 51/47* | (2006.01) |
| *B01D 61/02* | (2006.01) |
| *B01D 61/08* | (2006.01) |

(52) U.S. Cl.
CPC ............ *C07C 51/47* (2013.01); *B01D 61/026* (2022.08); *B01D 61/08* (2013.01); *B01D 2317/027* (2013.01); *B01D 2317/06* (2013.01)

(58) Field of Classification Search
CPC ...... C07C 51/47; B01D 61/026; B01D 61/08; B01D 2317/027; B01D 2317/06
See application file for complete search history.

(56) References Cited

U.S. PATENT DOCUMENTS

| | | | |
|---|---|---|---|
| 2,116,920 A | 5/1938 | Leonard |
| 3,216,930 A | 11/1965 | Glew |

(Continued)

FOREIGN PATENT DOCUMENTS

| | | |
|---|---|---|
| CA | 2785807 A1 | 7/2011 |
| CN | 101228214 A | 7/2008 |

(Continued)

OTHER PUBLICATIONS

Hydranautics—A Nitto Group Company, Pro Series-Specialty Membrane Products of Challenging Industrial Waste Waters, Pro-Series-Brochure (published online: May 18, 2020, pp. 1-4, URL: https://membranes.com/wp-content/uploads/Documents/brochure/PRO/PRO-Series-Brochure_web.pdf (Year: 2020).*

(Continued)

*Primary Examiner* — Yate' K Cutliff
(74) *Attorney, Agent, or Firm* — Dorsey & Whitney LLP

(57) ABSTRACT

Examples relate to systems and methods for concentrating acetic acid solutions using multi-tier ultrahigh pressure ("UHP") reverse osmosis. Along with an acetic acid product having a concentration of at least 25 weight percent (wt %), the systems and methods disclosed herein simultaneously provide water with an acetic acid concentration of 2 wt % or less in at little as three tiers.

18 Claims, 3 Drawing Sheets

(56)                References Cited

U.S. PATENT DOCUMENTS

| | | | |
|---|---|---|---|
| 3,352,422 A | 11/1967 | Goran | |
| 3,721,621 A | 3/1973 | Hough | |
| 4,326,509 A | 4/1982 | Usukura | |
| 4,428,720 A | 1/1984 | Van Erden et al. | |
| 4,454,176 A | 6/1984 | Buckfelder et al. | |
| 4,618,533 A | 10/1986 | Steuck | |
| 4,756,835 A | 7/1988 | Wilson | |
| 4,778,688 A | 10/1988 | Matson | |
| 4,900,443 A | 2/1990 | Wrasidlo | |
| 4,959,237 A | 9/1990 | Walker | |
| 5,084,220 A | 1/1992 | Moller | |
| 5,192,434 A | 3/1993 | Moller | |
| 5,238,574 A | 8/1993 | Kawashima et al. | |
| 5,281,430 A | 1/1994 | Herron et al. | |
| 5,593,738 A | 1/1997 | Ihm et al. | |
| 5,635,071 A * | 6/1997 | Al-Samadi | C02F 1/441 |
| | | | 210/651 |
| 6,261,879 B1 | 7/2001 | Houston et al. | |
| 6,406,626 B1 | 6/2002 | Murakami et al. | |
| 6,413,070 B1 | 7/2002 | Meyering et al. | |
| 6,513,666 B2 | 2/2003 | Meyering et al. | |
| 6,755,970 B1 | 6/2004 | Knappe et al. | |
| 6,849,184 B1 | 2/2005 | Lampi et al. | |
| 6,884,375 B2 | 4/2005 | Wang et al. | |
| 6,992,051 B2 | 1/2006 | Anderson | |
| 7,177,978 B2 | 2/2007 | Kanekar et al. | |
| 7,205,069 B2 | 4/2007 | Smalley et al. | |
| 7,445,712 B2 | 11/2008 | Herron | |
| 7,611,628 B1 | 11/2009 | Hinds, III | |
| 7,627,938 B2 | 12/2009 | Kim et al. | |
| 7,799,221 B1 | 9/2010 | Macharg | |
| 7,879,243 B2 | 2/2011 | Al-Mayahi et al. | |
| 7,901,578 B2 | 3/2011 | Pruet | |
| 7,955,506 B2 | 6/2011 | Bryan et al. | |
| 8,029,671 B2 | 10/2011 | Cath et al. | |
| 8,029,857 B2 | 10/2011 | Hoek et al. | |
| 8,038,887 B2 | 10/2011 | Bakajin et al. | |
| 8,083,942 B2 | 12/2011 | Cath et al. | |
| 8,177,978 B2 | 5/2012 | Kurth et al. | |
| 8,181,794 B2 | 5/2012 | Mcginnis et al. | |
| 8,221,629 B2 | 7/2012 | Al-Mayahi et al. | |
| 8,246,791 B2 | 8/2012 | Mcginnis et al. | |
| 8,252,350 B1 | 8/2012 | Cadwalader et al. | |
| 8,356,717 B2 | 1/2013 | Waller, Jr. et al. | |
| 8,518,276 B2 | 8/2013 | Stiemer et al. | |
| 8,567,612 B2 | 10/2013 | Kurth et al. | |
| 8,920,654 B2 | 12/2014 | Revanur et al. | |
| 8,960,449 B2 | 2/2015 | Tomioka et al. | |
| 9,216,391 B2 | 12/2015 | Revanur et al. | |
| 9,227,360 B2 | 1/2016 | Lulevich et al. | |
| 9,636,635 B2 | 5/2017 | Benton et al. | |
| 9,861,937 B2 | 1/2018 | Benton et al. | |
| 11,090,611 B2 | 8/2021 | Benton et al. | |
| 11,541,352 B2 | 1/2023 | Benton et al. | |
| 2001/0006158 A1 | 7/2001 | Ho et al. | |
| 2002/0063093 A1 | 5/2002 | Rice et al. | |
| 2002/0148769 A1 | 10/2002 | Deuschle et al. | |
| 2003/0038074 A1 | 2/2003 | Patil | |
| 2003/0141250 A1 | 7/2003 | Kihara et al. | |
| 2003/0173285 A1 | 9/2003 | Schmidt et al. | |
| 2003/0205526 A1 | 11/2003 | Vuong | |
| 2004/0004037 A1 | 1/2004 | Herron | |
| 2004/0071951 A1 | 4/2004 | Jin | |
| 2004/0084364 A1 | 5/2004 | Kools | |
| 2005/0016922 A1 | 1/2005 | Enzweiler et al. | |
| 2005/0056590 A1 | 3/2005 | Baggott et al. | |
| 2005/0142385 A1 | 6/2005 | Jin | |
| 2005/0166978 A1 | 8/2005 | Brueckmann et al. | |
| 2006/0144789 A1 | 7/2006 | Cath et al. | |
| 2006/0233694 A1 | 10/2006 | Sandhu et al. | |
| 2007/0181473 A1 | 8/2007 | Manth et al. | |
| 2007/0215544 A1 | 9/2007 | Kando et al. | |
| 2007/0246426 A1 | 10/2007 | Collins | |
| 2008/0017578 A1 | 1/2008 | Childs et al. | |
| 2008/0149561 A1 | 6/2008 | Chu et al. | |
| 2008/0210370 A1 | 9/2008 | Smalley et al. | |
| 2008/0223795 A1 | 9/2008 | Bakajin et al. | |
| 2008/0236804 A1 | 10/2008 | Cola et al. | |
| 2008/0237126 A1 | 10/2008 | Hoek et al. | |
| 2008/0290020 A1 | 11/2008 | Marand et al. | |
| 2009/0078640 A1 | 3/2009 | Chu et al. | |
| 2009/0214847 A1 | 8/2009 | Maruyama et al. | |
| 2009/0250392 A1 | 10/2009 | Thorsen et al. | |
| 2009/0272692 A1 | 11/2009 | Kurth et al. | |
| 2009/0283475 A1 | 11/2009 | Hylton et al. | |
| 2009/0308727 A1 | 12/2009 | Kirts | |
| 2009/0321355 A1 | 12/2009 | Ratto et al. | |
| 2010/0018921 A1 | 1/2010 | Ruehr et al. | |
| 2010/0025330 A1 | 2/2010 | Ratto et al. | |
| 2010/0032377 A1 | 2/2010 | Wohlert | |
| 2010/0051538 A1 | 3/2010 | Freeman et al. | |
| 2010/0059433 A1 | 3/2010 | Freeman et al. | |
| 2010/0062156 A1 | 3/2010 | Kurth et al. | |
| 2010/0140162 A1 | 6/2010 | Jangbarwala | |
| 2010/0155333 A1 | 6/2010 | Husain et al. | |
| 2010/0192575 A1 | 8/2010 | Al-Mayahi et al. | |
| 2010/0206743 A1 | 8/2010 | Sharif et al. | |
| 2010/0206811 A1 | 8/2010 | Ng et al. | |
| 2010/0212319 A1 | 8/2010 | Donovan | |
| 2010/0224550 A1 | 9/2010 | Herron | |
| 2010/0224561 A1 | 9/2010 | Marcin | |
| 2010/0297429 A1 | 11/2010 | Wang et al. | |
| 2010/0320140 A1 | 12/2010 | Nowak et al. | |
| 2010/0326833 A1 | 12/2010 | Messalem et al. | |
| 2011/0017666 A1 | 1/2011 | Cath et al. | |
| 2011/0036774 A1 | 2/2011 | Mcginnis | |
| 2011/0073540 A1 | 3/2011 | Mcginnis et al. | |
| 2011/0132834 A1 | 6/2011 | Tomioka et al. | |
| 2011/0133487 A1 | 6/2011 | Oklejas, Jr. | |
| 2011/0155666 A1 | 6/2011 | Prakash et al. | |
| 2011/0186506 A1 | 8/2011 | Ratto et al. | |
| 2011/0198285 A1 | 8/2011 | Wallace | |
| 2011/0203994 A1 | 8/2011 | Mcginnis et al. | |
| 2011/0220574 A1 | 9/2011 | Bakajin et al. | |
| 2011/0284456 A1 | 11/2011 | Brozell et al. | |
| 2011/0311427 A1 | 12/2011 | Hauge et al. | |
| 2012/0008038 A1 | 1/2012 | Yen et al. | |
| 2012/0012511 A1 | 1/2012 | Kim et al. | |
| 2012/0043274 A1 | 2/2012 | Chi et al. | |
| 2012/0080378 A1 | 4/2012 | Revanur et al. | |
| 2012/0080381 A1 | 4/2012 | Wang et al. | |
| 2012/0103892 A1 | 5/2012 | Beauchamp et al. | |
| 2012/0118743 A1 | 5/2012 | Liang et al. | |
| 2012/0118826 A1 | 5/2012 | Liberman et al. | |
| 2012/0118827 A1 | 5/2012 | Chang et al. | |
| 2012/0132595 A1 | 5/2012 | Bornia | |
| 2012/0152841 A1 | 6/2012 | Vissing et al. | |
| 2012/0160753 A1 | 6/2012 | Vora et al. | |
| 2012/0231535 A1 | 9/2012 | Herron et al. | |
| 2012/0234758 A1 | 9/2012 | Mcginnis et al. | |
| 2012/0241371 A1 | 9/2012 | Revanur et al. | |
| 2012/0241373 A1 | 9/2012 | Na et al. | |
| 2012/0251521 A1 | 10/2012 | Rostro et al. | |
| 2012/0261321 A1 | 10/2012 | Han et al. | |
| 2012/0267297 A1 | 10/2012 | Iyer | |
| 2012/0273421 A1 | 11/2012 | Perry et al. | |
| 2012/0298381 A1 | 11/2012 | Taylor | |
| 2013/0001162 A1 | 1/2013 | Yangali-Quintanilla et al. | |
| 2013/0095241 A1 | 4/2013 | Lulevich et al. | |
| 2013/0105383 A1 | 5/2013 | Tang et al. | |
| 2013/0126431 A1 | 5/2013 | Henson et al. | |
| 2013/0203873 A1 | 8/2013 | Linder et al. | |
| 2013/0220581 A1 | 8/2013 | Herron et al. | |
| 2013/0220927 A1 | 8/2013 | Moody et al. | |
| 2013/0264285 A1 | 10/2013 | Macintosh et al. | |
| 2014/0015159 A1 | 1/2014 | Lazar et al. | |
| 2014/0175011 A1 | 6/2014 | Benton et al. | |
| 2014/0302579 A1 | 10/2014 | Boulanger et al. | |
| 2014/0319056 A1 | 10/2014 | Fuchigami et al. | |
| 2015/0014232 A1 | 1/2015 | Mcginnis et al. | |
| 2015/0014248 A1 | 1/2015 | Herron et al. | |
| 2015/0064306 A1 | 3/2015 | Tatera et al. | |
| 2015/0273399 A1 | 10/2015 | Roh et al. | |
| 2016/0002074 A1 | 1/2016 | Benton et al. | |

(56) References Cited

U.S. PATENT DOCUMENTS

| 2016/0038880 A1 | 2/2016 | Benton et al. |
| 2016/0136577 A1 | 5/2016 | Mcgovern et al. |
| 2016/0136578 A1 | 5/2016 | Mcgovern et al. |
| 2016/0136579 A1 | 5/2016 | Mcgovern et al. |
| 2016/0230133 A1 | 8/2016 | Peterson et al. |
| 2017/0121190 A1 | 5/2017 | Ikuno |
| 2017/0190650 A1 | 7/2017 | Peterson et al. |
| 2017/0197181 A1 | 7/2017 | Benton et al. |
| 2017/0232392 A1 | 8/2017 | Desormeaux et al. |
| 2017/0333847 A1 | 11/2017 | Lulevich et al. |
| 2018/0311618 A1 | 11/2018 | Benton et al. |
| 2020/0024557 A1 | 1/2020 | Benton et al. |
| 2020/0086274 A1 | 3/2020 | Benton et al. |
| 2020/0094193 A1 | 3/2020 | Benton et al. |
| 2021/0339201 A1 | 11/2021 | Benton et al. |
| 2023/0149853 A1 | 5/2023 | Benton et al. |

FOREIGN PATENT DOCUMENTS

| CN | 102642894 A | 8/2012 |
| CN | 102674605 A | 9/2012 |
| CN | 105142762 A | 12/2015 |
| CN | 107922220 A | 4/2018 |
| EP | 1894612 A1 | 3/2008 |
| EP | 3181215 A1 | 6/2017 |
| FR | 2189091 A1 | 1/1974 |
| JP | S55149682 A | 11/1980 |
| JP | 59059213 A | 4/1984 |
| JP | S5959213 A | 4/1984 |
| JP | 62-140620 A | 6/1987 |
| JP | 2005-138028 A | 6/2005 |
| JP | 2010094641 A | 4/2010 |
| JP | 2012183492 A | 9/2012 |
| JP | 2013081922 A | 5/2013 |
| JP | 2013128874 A | 7/2013 |
| KR | 101144316 B1 | 5/2012 |
| KR | 101229482 B1 | 2/2013 |
| WO | 1993/010889 | 6/1993 |
| WO | 9413159 A1 | 6/1994 |
| WO | 9962623 | 12/1999 |
| WO | 0213955 A1 | 2/2002 |
| WO | 2006040175 A1 | 4/2006 |
| WO | 2008/137082 A1 | 11/2008 |
| WO | 2009/035415 | 3/2009 |
| WO | 2009039467 A1 | 3/2009 |
| WO | 2009104214 A1 | 8/2009 |
| WO | 2009129354 A2 | 10/2009 |
| WO | 2010002165 A2 | 1/2010 |
| WO | 2010006196 A2 | 1/2010 |
| WO | 2010050421 A1 | 5/2010 |
| WO | 2010067063 A1 | 6/2010 |
| WO | 2010067065 A1 | 6/2010 |
| WO | 2010144057 A1 | 12/2010 |
| WO | 2011028541 A2 | 3/2011 |
| WO | 2011155338 A1 | 12/2011 |
| WO | 2012/047282 | 4/2012 |
| WO | 2012/084960 | 6/2012 |
| WO | 2012095506 A1 | 7/2012 |
| WO | 2012102677 A1 | 8/2012 |
| WO | 2012/135065 | 10/2012 |
| WO | 2013/022945 A2 | 2/2013 |
| WO | 2013032742 A1 | 3/2013 |
| WO | 2013/059314 | 4/2013 |
| WO | 2014063149 A1 | 4/2014 |
| WO | 2014/071238 A1 | 5/2014 |
| WO | 2014100766 A2 | 6/2014 |
| WO | 2014144704 A1 | 9/2014 |
| WO | 2014144778 A1 | 9/2014 |
| WO | WO2014144778 | 9/2014 |
| WO | 2015157818 A1 | 10/2015 |
| WO | 2016022954 A1 | 2/2016 |
| WO | 2016070103 A1 | 5/2016 |
| WO | 2016094835 A1 | 6/2016 |
| WO | 2016210337 A2 | 12/2016 |
| WO | 2018119460 A1 | 6/2018 |
| WO | 2018200538 A1 | 11/2018 |
| WO | 2019113335 A1 | 6/2019 |
| WO | 2022060747 | 3/2022 |

OTHER PUBLICATIONS

App. No. PCT/US17/68345, "Removing Components of Alcoholic Solutions Via Forward Osmosis and Related Systems"; filed on Dec. 22, 2017.

English translation of Examination Report for IN Application No. 201817001260, dated Mar. 6, 2020.

English Translation of Final Rejection for CN Application No. 201480022732.9 dated Jun. 26, 2018.

English translation of KR Notice of Preliminary Rejection for Application No. 10-2015-7019175, dated Jan. 22, 2020.

English translation of Office Action for BR Application No. 1120150147763, mailed Apr. 8, 2021.

English translation of Office Action for CN Application No. 201680045242, dated Apr. 8, 2021.

English translation of Office Action for CN Application No. 201680045242.X, dated Jul. 15, 2020.

English translation of Office Action for CN Application No. 201780086041.9, mailed May 8, 2021.

Examination Report No. 2 dated Apr. 6, 2018 for Australian application No. 2014228787, 3 pages.

Extended EP search report & Written Opinion dated May 15, 2015 for EP appln No. 11831039.0.

Extended European Search Report for EP Application No. 16815432.6 dated Dec. 19, 2018.

Extended European Search Report for EP Application No. 17882858.8 dated Aug. 17, 2020.

Extended European Seatch Report received for EP Appl. No. 14764413.2 dated Feb. 8, 2017.

First OA for KR Application No. 10-2013-7011268 dated Feb. 19, 2018.

First OA, JP Application No. 2016-198872, dated Aug. 15, 2017.

First Office Action dated Jul. 14, 2015 received for JP Appln No. 2013-531565.

First Office Action; EP Application No. 11831039.0, dated Sep. 21, 2017.

Fourth OA for CN Application No. 201480022732.9, dated Dec. 28, 2017.

International Search Report and Written Opinion dated Feb. 22, 2018 for PCT Application No. PCT/US2017/068345.

International Search Report and Written Opinion for app. No. PCT/US2014/029227 dated Jul. 1, 2014.

International Search Report and Written Opinion for app. No. PCT/US2014/029332 dated Jul. 3, 2014.

International Search Report and Written Opinion for Appl No. PCT/US2013/077314, Mailed Apr. 28, 2014.

IP Australia Patent Examination Report No. 1 for Appl. No. 2011312881 issued Sep. 12, 2014.

Office Action dated Jul. 27, 2020 for EP Application No. 13865011.4.

Office Action dated Sep. 20, 2018 for EP Application No. 13865011.4.

Office Action for AU Application No. 2016283127, dated Nov. 20, 2020.

Office Action for BR Application No. BR1120150147763, dated Oct. 2, 2019.

Office Action for CA Application No. 3,011,833, dated Oct. 4, 2019.

Office Action for EP Application No. 14764413.2, dated Mar. 9, 2021.

Office Action for Israel Application No. 225,462 dated Oct. 15, 2017.

PCT Application PCT/US21/50330 titled "Methods and Systems for Concentrating Acetic Acid Solutions With a Multi-Tier, Ultrahigh Pressure Reverse Osmosis" filed Sep. 14, 2021.

Second Office Action for CN Application No. 201480025277.8, dated Jul. 3, 2017.

Second Office Action for IL Application No. 239528, dated Apr. 25, 2018.

(56)                 References Cited

OTHER PUBLICATIONS

Summary of First Office Action dated Jul. 8, 2019 for Chilean Patent Application No. 201703297, 10 pages.
Third OA for CN Application No. 201480022732.9, dated Jun. 29, 2017.
Third Office Action dated Jul. 11, 2017 for Japanese application No. 2013-531565.
Third Office Action; CA Application No. 2,896,047, dated Aug. 9, 2018.
U.S. Appl. No. 18/165,162 titled, "Methods of Dewatering of Alcoholic Solutions via Forward Osmosis Andrelated Systems," filed Feb. 6, 2023.
U.S. Appl. No. 15/470,757, entitled "Separation Systems, Elements, and Methods for Separation Utilizing Stacked Membranes and Spacers", filed Mar. 27, 2017.
U.S. Appl. No. 15/522,701, entitled "Supported Carbon Nanotube Membranes and Their Preparation Methods", filed Apr. 27, 2017.
U.S. Appl. No. 15/739,657, Methods of Dewatering of Alcoholic Solutions via Forward Osmosis and Related Systems, filed Dec. 22, 2017.
U.S. Appl. No. 16/473,088 titled "Methods of Dewatering of Alcoholic Solutions via Forward Osmosis and Related Systems" filed Dec. 22, 2017.
"English Translation of Office Action for CN 201780086041.9, mailed Jan. 6, 2022".
"English translation of Office Action for CN Application No. 201680045242.X, dated Sep. 2, 2021".
"English Translation of Office Action mailed Jul. 13, 2022 for CL Appl. No. 3297-2017".
"European Patent Office OL to Proceed for European Pat. Appl. No. 13865011.4 dated Aug. 12, 2016".
"European Search Report received for PCT/US2013077314 dated Jul. 27, 2016".
"Examination Report for AU Patent App. No. 2021204374, mailed on Apr. 21, 2022".
"Examination Report for EP 13865011.4, mailed on Dec. 6, 2022".
"Examination Report for EP 17882858.8, issued on Oct. 25, 2021".
"Examination Report for Israeli Patent Appl. No. 25462 dated Aug. 24, 2016".
"Examination Report No. 1 dated May 15, 2017 for Australian application No. 2014228787, 4 pages."
"Extended European Seatch Report receivedfor EP Appl. No. 14764413.2 dated Jan. 2, 2017".
"First Office Action for CN Application No. 201480025277.8 dated Jul. 29, 2016".
"First Office Action for PRC (China) Pat. Appln. No. 201480022732.9 dated Jul. 5, 2016".
"First Office Action Issued by State Intellectual Property Office for PCT Application No. 201380071624.6 dated May 5, 2016".
"First Office Action of the China State Intellectual Property Office for CN Application No. 201180047473.1 mailed on Sep. 2, 2014".
"First office action received for Australian application No. 2013364069 dated May 2, 2017".
"First Office Action received for Canadian Application No. 2896047 dated Jul. 7, 2016".
"Guide To Forward Osmosis Membranes", ForwardOsmosisTech, https://www.forwardosmosistech.com/forward-osmosis-membranes/ (last visited Aug. 19, 2020)., 2020, 1-6.
"Hydranautics—A Nitto Group Company, "Pro Series-Specialty Membrane Products for Challenging Industrial Wastewaters"", Pro-Series-Brochure (published online: May 18, 2020); pp. 1-4 (p. 2, col. 2, paragraph 2); URL: https://membranes.com/wp-content/uploads/Documents/brochure/PRO/PRO-Series-Brochure_web.pdf, May 18, 2020.
"International Search and Written Opinion received for PCT US2015/58417 dated Feb. 3, 2016".
"International Search Report & Written Opinion for Appl No. PCT/US2013/068143 dated Jan. 24, 2014".
"International Search Report and Written Opinion for PCT/US2021/050330, mailed Dec. 29, 2021".
"International Search Report and Written Opinion received for PCT Appl. No. PCT/US2016/039377 dated Jan. 19, 2017".
"International Search Report and Written Opinion received for PCT/US2015/044277 dated Oct. 23, 2015".
"Notice of Hearing for IN Appl. No. 2023/KOLNP/2015, mailed on Dec. 20, 2022".
"Osmotic Pressure and Solutions", Center for Student Success and Academic Counseling, The University of North Carolina at Chapel Hill, http://cssac.unc.edu/programs/learning-center/Resources/Study/Guides/Chemistry%20102/Osmotic%20Pressure, accessed Jan. 20, 2021.
"Patent Search Report".
"Preliminary Office Action recevied for app. # 239528 dated Feb. 4, 2017".
"Search Report and WO", Search Report and Written Opinion dated Mar. 29, 2013 for Appl No. PCT/US2012/060607.
"Search Report and WO", Search Report and Written Opinion dated May 1, 2012 for Appl No. PCT/US2011/001701.
"Search Report and WO", Search Report and Written Opinion dated Oct. 31, 2012 for Appl No. PCT/US2012/030449.
"Second Office Action for Japanese Patent Application No. 2013-531565, dated Jun. 7, 2016".
"Second Office Action for PRC (China) Pat. Appln. No. 201480022732.9 dated Jan. 16, 2017".
"Second office action received for application No. 2,896,047 dated May 1, 2017".
"Summany of Office Action mailed Jul. 8, 2019, for CL3297-2017".
"Summons to Attend Oral Proceedings for EP 16815432.6, mailed Jul. 9, 2021".
"Translation for Rejection Decision, mailed Jun. 28, 2022, for CN 201780086041.9".
Akthakul , et al., "Antifouling polymer membranes with subnanometer size selectivity", Macromolecules 37, Sep. 3, 2004, 7663-7668.
Beibei , et al., "(Category A—No Translation—do not cite per client) Preparation of Thin Film Composite Membrane by Interfacial Polymerization Method", Progress in Chemistry, vol. 19, No. 9, Sep. 30, 2007, 1-8.
Blandin , et al., "Validation of assisted forward osmosis (AFO) process: Impact of hydraulic pressure", Journal of Membrane Science vol. 447, pp. 1-11, Jun. 2013.
Canadian IP Office , "Office Action", Application No. 2,896,047, Jul. 9, 2019, 4 pages.
Cath , et al., "Forward osmosis: principles, applications and recent developments", Journal of Membrane Science 281, May 31, 2006, 70-87.
Chen , et al., Influences of molecular weight, molecular size, flux, and recovery for aromatic pesticide removal by nanofiltration membranes, Jan. 2004, Desalination 160, pp. 103-111.
Ge, Qingchun , et al., "Draw Solutions for Forward Osmosis Processes: Developments, Challenges, and Prospects for the Future", Journal of Membrane Science, vol. 442, issued Apr. 6, 2013, pp. 225-237.
Israel Patent Office , "Office Action", Application No. 264433, Aug. 25, 2019, 4 pages.
Ju , et al., "Effect of monomer structure on separation property of polyamides composite membrane", Macromolecule Transactions, No. 2, Apr. 30, 2006.
Li , et al., "Electronic properties of multiwalled carbon nanotubes in an embedded vertical array", Applied Physics Letters vol. 81, No. 5, Jul. 2002, 910-912.
Low , et al., ""Challenges in membrane-based liquid phase separations"", Green Chemical Engineering, vol. 2, Issue 1 (Mar. 2021), pp. 3-13.
Mandal , et al., "Drug delivery system based on chronobiology—a review", Journal of Controlled Release 147, Aug. 4, 2010, 314-325.
Mccutcheon , et al., "Influence of membrane support layer hydrophobicity on water flux in osmotically driven membrane processes", Journal of Membrane Science, Mar. 2008, 458-466.
Mceuen Paul, et al., "Single-Walled Nanotubes Electronics", IEEE Transactions on Nanotechnology, Vo. 1, No. 1, Mar. 2002.
Qingchun, Ge , et al., "Draw solutions for forward osmosis processes: Developments, challenges, and prospects for the future", Journal of Membrane Science, vol. 442, Sep. 1, 2013, pp. 225-237.

(56)         References Cited

OTHER PUBLICATIONS

Santus , et al., "Osmotic drug delivery: a review of the patent literature", Journal of Controlled Release 35, Jul. 1995, 1-21.

Shon, Ho Kyong, et al., "Introduction: Role of Membrane Science and Technology And Forward Osmosis Processes", https://app.knovel.com/hotlink/toc/id:kpFOFA0001/forward-osmosis-fundamentals/forward-osmosis-fundamentals, 2015, pp. 1, 5-6.

Sotthivirat , et al., "Controlled porosity-osmotic pump pellets of a poorly water-soluble drug using sulfobutylether-b-cyclodestrin, (SBE)_7M-b-CD, as a solubilizing and osmotic agent", Journal of Pharmaceutical Sciences vol. 96, No. 9, Sep. 2007, 2364-2374.

Yip , et al., "High performance Thin-Film Composite Forward Osmosis Membrane", Environmental Science andTechnology vol. 44, Apr. 21, 2010, 3812-3818.

Zhao , et al., "Modification of porous poly (vinylidene fluoride) membrane using amphiphilic polymers with different structures in phase inversion process", Journal of Membrane Science 310, Mar. 2008, 567-576.

"Office Action for CA Appl. No. 3,048,017, mailed on Jan. 30, 2024 pgs. all".

* cited by examiner

300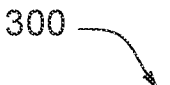

| |
|---|
| Subjecting a feed stream including an acetic acid solution to a first ultrahigh pressure reverse osmosis process to form a first concentrate stream and a first permeate stream |

*310*

| |
|---|
| Subjecting the first concentrate stream to a second ultrahigh pressure reverse osmosis process to form a second concentrate stream and a second permeate stream |

*320*

| |
|---|
| Subjecting the first permeate stream to a third ultrahigh pressure reverse osmosis process to form a third permeate stream and a third concentrate stream |

METHODS AND SYSTEMS FOR CONCENTRATING ACETIC ACID SOLUTIONS WITH A MULTI-TIER, ULTRAHIGH PRESSURE REVERSE OSMOSIS

CROSS-REFERENCE TO RELATED APPLICATION

This application is a 35, U.S.C. § 371 National Stage Application of PCT Application No. PCT/US2021/050330, filed Sep. 24, 2021, which claims priority to U.S. Provisional Application No. 63/078,518 filed on 15 Sep. 2020, the disclosure of which is incorporated herein in its entirety by this reference.

BACKGROUND

Acetic acid is a carboxylic acid commonly present in foods and food production processes. Acetic acid is often used as a descaling agent. At higher concentrations, acetic acid can be harsh on processing equipment, causing corrosion. At higher concentrations, acetic acid can be harmful to the health of humans causing eye irritation, skin irritation, headache, fever, breathing difficulties, and damage to internal organs.

Acetic acid is commonly concentrated from vinegar using distillation. However, such a process is not cost or energy efficient. Further, distillation of acetic acid solutions requires specialized equipment and chemicals. Accordingly, those who work with acetic acid continue to search for effective strategies for processing acetic acid.

SUMMARY

Embodiments of the invention relate to concentrating acetic acid solutions using multi-tier ultrahigh pressure ("UHP") reverse osmosis. Along with an acetic acid product having a concentration of at least 25 weight percent (wt %), the systems and methods disclosed herein simultaneously provide water with an acetic acid concentration of 2 wt % or less.

In an embodiment, a method for concentrating acetic acid solutions is disclosed. The method includes subjecting a feed stream including an acetic acid solution to a first ultrahigh pressure reverse osmosis process to form a first concentrate stream and a first permeate stream. The method includes subjecting the first concentrate stream to a second ultrahigh pressure reverse osmosis process to form a second concentrate stream and a second permeate stream. The method includes subjecting the first permeate stream to a third ultrahigh pressure reverse osmosis process to form a third permeate stream and a third concentrate stream.

In an embodiment, a system for concentrating acetic acid solutions is disclosed. The system includes a first ultrahigh pressure reverse osmosis membrane module array configured to receive a feed stream including an acetic acid solution and produce a first concentrate stream and a first permeate stream. The system includes a second ultrahigh pressure reverse osmosis membrane module array configured to receive the first concentrate stream and produce a second concentrate stream and a second permeate stream. The system includes a third ultrahigh pressure reverse osmosis membrane module array configured to receive the first permeate stream and produce a third concentrate stream and a third permeate stream.

In an embodiment, a method for concentrating acetic acid solutions is disclosed. The method includes circulating a feed stream including an acetic acid solution through a first ultrahigh pressure reverse osmosis membrane module array at a first pressure of at least 1500 psi to form a first concentrate stream and a first permeate stream. The method includes circulating the first concentrate stream through a second ultrahigh pressure reverse osmosis membrane module array at a second pressure of at least 1500 psi to form a second concentrate stream and a second reverse osmosis permeate. The method includes circulating the first permeate stream through a third ultrahigh pressure reverse osmosis membrane module array at a third pressure of at least 1500 psi to form a third permeate stream and a third reverse osmosis concentrate.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, the like elements have been designated by like reference numbers throughout the various accompanying figures. Understanding that these drawings depict only typical embodiments of the invention and are not therefore to be considered to be limiting of its scope, the embodiments of the invention will be described and explained with additional specificity and detail through the use of the accompanying drawings in which:

FIG. 3 is a flow chart of a method for concentrating an acetic acid solution, according to at least some embodiments.

DETAILED DESCRIPTION

Embodiments described herein relate to methods, devices, and systems disclosed herein that utilize ultrahigh pressure reverse osmosis to concentrate acetic acid solutions (e.g., vinegar) in a minimum of three tiers of ultrahigh pressure reverse osmosis membrane module arrays. Ultra high pressure reverse osmosis utilizes reverse osmosis membranes and modules that can withstand and operate at "ultrahigh pressures" between 1200 psi (8.3 MPa) and 2000 psi (13.8 MPa), such as at least 1750 psi (12.1 MPa). By utilizing at least three tiers of ultrahigh pressure (UHP) reverse osmosis (RO) membrane module arrays using ultrahigh pressure membranes and operating at ultrahigh pressures, users can obtain a final concentrate stream comprising at least 25 wt % acetic acid (e.g., at least 30 wt %) and a final permeate product comprising no more than 2 wt % (e.g., 1 wt % or less).

Figure 1:
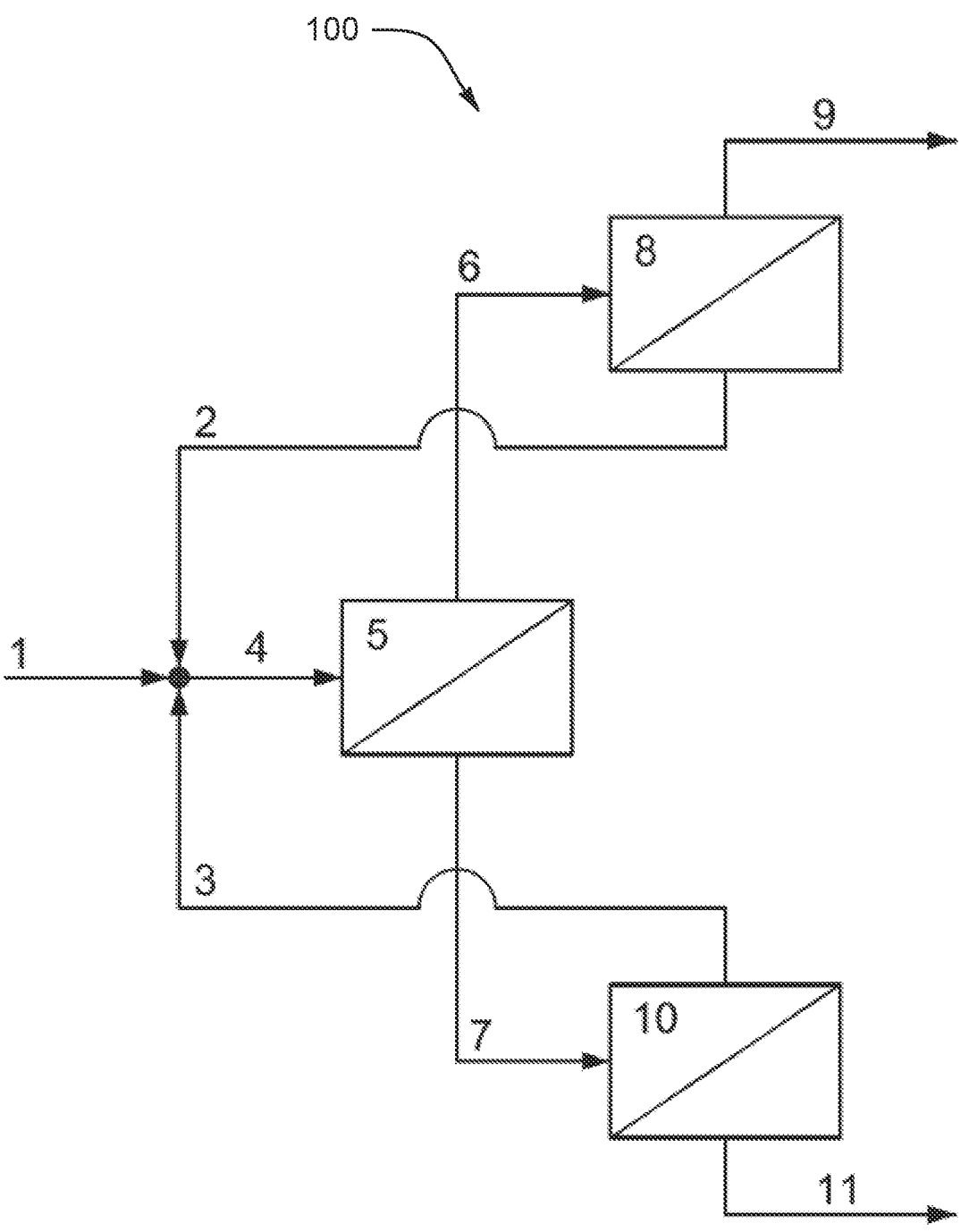
FIG. 1 is a schematic of a multi-tiered system for concentrating acetic acid solutions, according to at least some embodiments.

FIG. 1 is a schematic of a multi-tiered system 100 for concentrating acetic acid solutions, according to at least some embodiments. The system 100 depicted in FIG. 1 includes a first reverse osmosis (RO) membrane module array 5, a second RO membrane module array 8, and a third RO membrane module army 10. The RO membrane module arrays disclosed herein are UHP RO membrane module arrays unless context dictates otherwise. A concentration of an acetic acid solution entering a first tier or first RO membrane module array 5 may be concentrated to produce a concentrated acetic acid solution product in the second RO membrane module array 8, and a purified water product in the third RO membrane module array 10.

Various streams of liquids are connected to the various RO membrane modules arrays, such as via conduits connected thereto. For example, a feed stream 1 is connected to the first RO membrane module array 5, such as via the combined stream 4 (combination of the feed stream 1 and one or more of permeate stream 2 or concentrate stream 3). The second RO membrane module array 8 may be fluidly connected to the concentrate stream 6 rejected from the first RO membrane module array 5 and the third RO membrane module array 10 may be fluidly connected to the permeate stream 7 of the first RO membrane module array 5. The various RO membrane module arrays and streams are fluidly connected via one or more conduits (e.g., tubes, pipes, etc.).

Each of the RO membrane module arrays may independently include one or more (UHP) RO membrane modules arranged in series or in parallel. The (UHP) RO membrane modules include an RO membrane capable of withstanding hydrostatic pressure in excess of 1200 psi (8.3 MPa), such as between 1200 psi (8.3 MPa) and 2000 psi (13.8 MPa), 1500 psi (10.3 MPa) to 1750 psi (12.1 MPa), 1750 psi (12.1 MPa) to 2000 psi (13.8 MPa), or at least 1500 psi (10.3 MPa). Suitable RO membranes include DOW™ Specialty Membrane XUS180804 and XUS180802, and HYDRANU- ATICS (Nitto Group Company) PRO-XS1, PRO-XS3, PRO-LF1, and PRO-XP reverse osmosis membranes. The RO membrane separates a feed and reject side from a permeate side in a respective RO membrane module. The (UHP) RO membrane modules include a fluid tight housing capable of withstanding ultrahigh pressures without leaking, a feed inlet, an RO permeate outlet, and an RO concentrate outlet. The total membrane area of the RO membrane modules and/or arrays in the different tiers may differ to provide different flux rates in the respective tiers. For example, membrane modules and arrays receiving solutions with greater concentrations of acetic acid may have relatively larger membrane areas than membrane modules and arrays receiving streams with relatively lower concentrations of acetic acid. In such examples, the first RO membrane module array 5 may have a first membrane area, the second RO membrane module array 8 may have more membrane area than the first RO membrane module array 5 (to process the higher concentration of acetic acid in the concentrate stream 6, and the third RO membrane module array 10 may have less membrane area than the first RO membrane module array 5 (to process the lower concentration of acetic acid in the permeate stream 7.

A feed stream 1 including an acetic acid solution having a first concentration of acetic acid may be introduced into the system at a first mass flow rate (e.g., at least 50 kg per minute). The acetic acid solution may include vinegar, such as a distilled or a filtered vinegar that includes mainly water and acetic acid (e.g., at a concentration range of 7-29 wt % acetic acid) and does not include significant amounts of dissolved or suspended solids that may be present in other types of vinegars, such as balsamic vinegar. Significant amounts (e.g., more than trace amounts) of dissolved or suspended solids, other than acetic acid and volatile organic chemicals, may reduce or even halt the performance of the process by changing the flow conditions for the process stream or by fouling the membranes.

The feed stream 1 may be combined with other streams prior to introduction into the first RO membrane module array 5. For example, feed stream 1 may be combined with permeate stream 2 composed of permeate from the second RO membrane module array 8 fluidly connected thereto. The permeate stream 2 may include a relatively lower concentration of acetic acid than feed stream 1 (e.g., less than 10 wt % acetic acid at a mass flow rate of less than 50 kg per minute) because permeate stream 2 is the permeate of the concentrate stream 6 from the first RO membrane module array 5 that has been processed in the second RO membrane module array 8. In some examples, the permeate stream 2 may include a substantially similar concentration of acetic acid compared to feed stream 1 (e.g., within 6 wt %). In such examples, the concentration of acetic acid in the permeate stream 2 may even be higher than in the feed stream 1. The feed stream 1 may be combined with concentrate stream 3 that is fluidly connected thereto. Concentrate stream 3 is the reject stream from the third RO membrane module array 10. Concentrate stream 3 may include may include a lower concentration of acetic acid than feed stream 1 (e.g., less than 10 wt % acetic acid at a mass flow rate of less than 50 kg per minute) because concentrate stream 3 is the reject of the permeate stream 7 from the first RO membrane module array 5 that has been processed in the third RO membrane module array 10. In some examples, the stream 3 may include a substantially similar concentration of acetic acid compared to the feed stream 1 (e.g., within 6 wt %). In such examples, the concentration of acetic acid in the stream 3 may even be higher than in the feed stream 1. Feed stream 1, permeate stream 2, and concentrate stream 3 combine to form combined stream 4. Combined stream 4 may have a lower acetic acid concentration than feed stream 1 but may have a higher acetic acid concentration than permeate stream 2 and concentrate stream 3. For example, combined stream 4 may have an acetic acid concentration of at least 11 wt % acetic acid. The mass flow rate of combined stream 4 may be the combination the mass flow rates of feed stream 1, permeate stream 2, and concentrate stream 3, such as at least 110 kg per minute. Combined stream 4 may be temperature controlled at this point, for example by a heat exchanger, to a temperature of between 2° C. and 30° C., 5° C. and 20° C., or 15° C. Combined stream 4 may be pressurized to an ultrahigh pressure, between 1200 psi (8.3 MPa) and 2000 psi (13.8 MPa), for example at least 1750 psi (12.1 MPa), and delivered to the first RO membrane module array 5, which may operate at flux between 5 LMH and 50 LMH, for example 24 LMH. Combined stream 4 may be pressurized by a pump (not shown), such as connected thereto prior to the first RO membrane module array 5.

The first RO membrane module array 5 may operate between 25% and 75% recovery by mass, for example 51% recovery by mass, rejecting 76% of the acetic acid, producing concentrate stream 6 (e.g., reject or concentrate stream of the first UHP reverse osmosis module array 5) including a higher concentration acetic acid solution than the combined stream 4 (e.g., at least 18 wt %). The mass flow rate of the concentrate stream 6 may be at least of 70 kg per minute. The first RO membrane module array 5 produces permeate stream 7, which may include a lower concentration of acetic acid than the concentrate stream 6 (e.g., less than 6 wt %). The mass flow rate of the permeate stream 7 may be at least 70 kg per minute and may be greater than the mass flow rate of the concentrate stream 6.

Concentrate stream 6 may be temperature controlled, for example by a heat exchanger not shown), to a temperature of between 2° C. and 30° C., 5° C. and 20° C., or about 15°

C. Concentrate stream 6 may be pressurized to an ultrahigh pressure, between 1200 psi (8.3 MPa) and 2000 psi (13.8 MPa), for example 1750 psi (12.1 MPa), and delivered to the second RO membrane module array 8, which may operate at flux between 5 LMH and 50 LMH, for example 16 LMH. The second RO membrane module array 8 may operate between 25% and 75% recovery by mass, for example 41% recovery by mass, rejecting at least 65% (e.g., 68%) of the acetic acid, producing a (second, product, or final) concentrate stream 9 having the highest concentration of acetic acid in the system of FIG. 1 (e.g., at least twice the concentration of combined stream 4, such as at least 25 wt %). The concentrate stream 9 may be produced at a mass flow rate of at least 40 kg per minute. The concentrate stream 9 is now at a final concentration, and leaves the system 100 of FIG. 1 to be collected, such as through a product line (e.g., pipe, conduit) or product tank. The second RO membrane module array 8 produces the (second) permeate stream 2 which may have a lower concentration of acetic acid than feed stream 1. Permeate stream 2 may be recycled back to the first RO membrane module array 5, such as being a portion of combined stream 4.

Permeate stream 7 from the first RO membrane module array 5 may be temperature controlled, for example by a heat exchanger, to a temperature of between 2° C. and 30° C., 5° C. and 20° C., or about 15° C. Permeate stream 7 may be pressurized to an ultrahigh pressure, between 1200 psi (8.3 MPa) and 2000 psi (13.8 MPa), for example at least 1750 psi (12.1 MPa), and delivered to the third RO membrane module array 10, which may operate at flux between 5 LMH and 50 LMH, for example 32 LMH. The Third RO membrane module array 10 may operate between 25% and 75% recovery by mass, for example 61% recovery by mass, rejecting at least 80% (e.g., 84%) of the acetic acid, producing (third) concentrate stream 3 and (third) permeate stream 11. The permeate stream 11 may include less than 2 wt % (e.g., 1.0 wt % or less) acetic acid. The permeate stream 11 may be produced at a mass flow rate of at least 45 kg per minute. The permeate stream 11 is now at a sufficiently low concentration to be discharged to waste water treatment or recycled back into an upstream process. Concentrate stream 3, which includes an acetic acid concentration of at least double the acetic acid concentration in the incoming permeate stream 7, may be produced at a mass flow rate of at least 25 kg per minute. The concentrate stream 3 may be recycled back to the first RO membrane module array 5, such as being a portion of combined stream 4.

While the pressure in each of the RO membrane module arrays is in the ultrahigh range (e.g., 1200 psi (8.3 MPa) to 2000 psi (13.8 MPa), 1200 psi (8.3 MPa) to 1500 psi (10.3 MPa), 1500 psi (10.3 MPa) to 1750 psi (12.1 MPa), 1500 psi (10.3 MPa) to 2000 psi (13.8 MPa), 1750 psi (12.1 MPa) to 2000 psi (13.8 MPa), at least 1500 psi (10.3 MPa), or at least 1750 psi (12.1 MPa)), the pressure in the third RO membrane module array 10 may be the lowest of the three tiers, and the pressure in the second RO membrane module array may be the highest of the three tiers to accommodate (e.g., provide the selected flux) for the concentrations of acetic acid in the streams fed thereto.

In examples, various alterations may be made to the system 100 of FIG. 1. For example, one or more pumps may be located at one or more points in the system 100 to control the pressures in the various streams.

The system 100 is particularly efficient at processing incoming feed streams 1 with acetic acid concentrations between about 7 wt % to 17 wt %. If the incoming feed steam 1 has a concentration of acetic acid outside of the range of 7 wt % to 17 wt %, the system 100 may be reconfigured to accommodate the different acetic acid concentration. For example, if the incoming feed stream 1 were relatively low (e.g., less than 7 wt %, such as 4 wt %), the system 100 may include a bypass to direct the feed stream 1 directly into the third RO membrane module array 10. In such examples, the remainder of the system 100 may be substantially identical. Accordingly, the concentrate stream 3 from the third RO membrane module array 10 may be directed to the first RO membrane module array 5. If the incoming feed stream 1 were relatively high (e.g., more than 17 wt %, such as 20 wt %), the system may include a bypass to direct the feed stream 1 directly to the second RO membrane module array 8. In such examples, the permeate stream 2 from the second RO membrane module array 8 may be directed to the first RO membrane module array 5. The bypasses may be located prior to the point at which the feed stream 1, stream 2, and stream 3 combine. Such bypasses may include conduits and valves to selectively control the direction of flow of the feed stream 1. In such examples, the streams 2 and 3 may still be combined with each other, and optionally, with a portion of feed stream 1, to provide the combined stream 4 to the first RO membrane module array 5.

Various concentrations of acetic acid feed streams may be concentrated utilizing the system 100 of FIG. 1. With the acetic acid rejection values in the 65-86% range with the ultrahigh pressure RO membrane modules and system 100, concentration of acetic acid solutions can be performed in 3 stages vs. 6 stages with conventional high pressure reverse osmosis. Due to the recirculation effect, the ultrahigh pressure RO processes and systems disclosed herein use approximately 6 time less equipment and 3 times less power than a 900 psi (6.2 MPa) reverse osmosis process.

Both the rejection and flux of the RO membranes is highly dependent on temperature and acetic acid concentration. As temperature increases, the flux increases and the rejection decreases. This effect is more extreme than in typical RO applications at lower pressures such as below 1200 psi (8.3 MPa). For this reason, temperature control may be utilized in the system 100 during operation. Such temperature control may be a determining factor in both the amount of required membrane area for a given flow rate, and the final concentrations achievable in both the concentrate stream 9 and permeate stream 11. The use of heat exchangers and temperature control systems may be used to control temperature within the system. For example, one or more heat exchangers may be positioned in the system 100 prior to the first UHP reverse osmosis membrane module array 5, prior to the membrane module array 8, or prior to the third membrane module array 10, such as fluidly connected to conduits containing the combined stream 4, the feed stream 1, the concentrate stream 3, or the concentrate stream 6.

In some examples, the systems disclosed herein may include plumbing and components to allow cleaning, testing, and recirculation of the various membrane module arrays.

Figure 2:
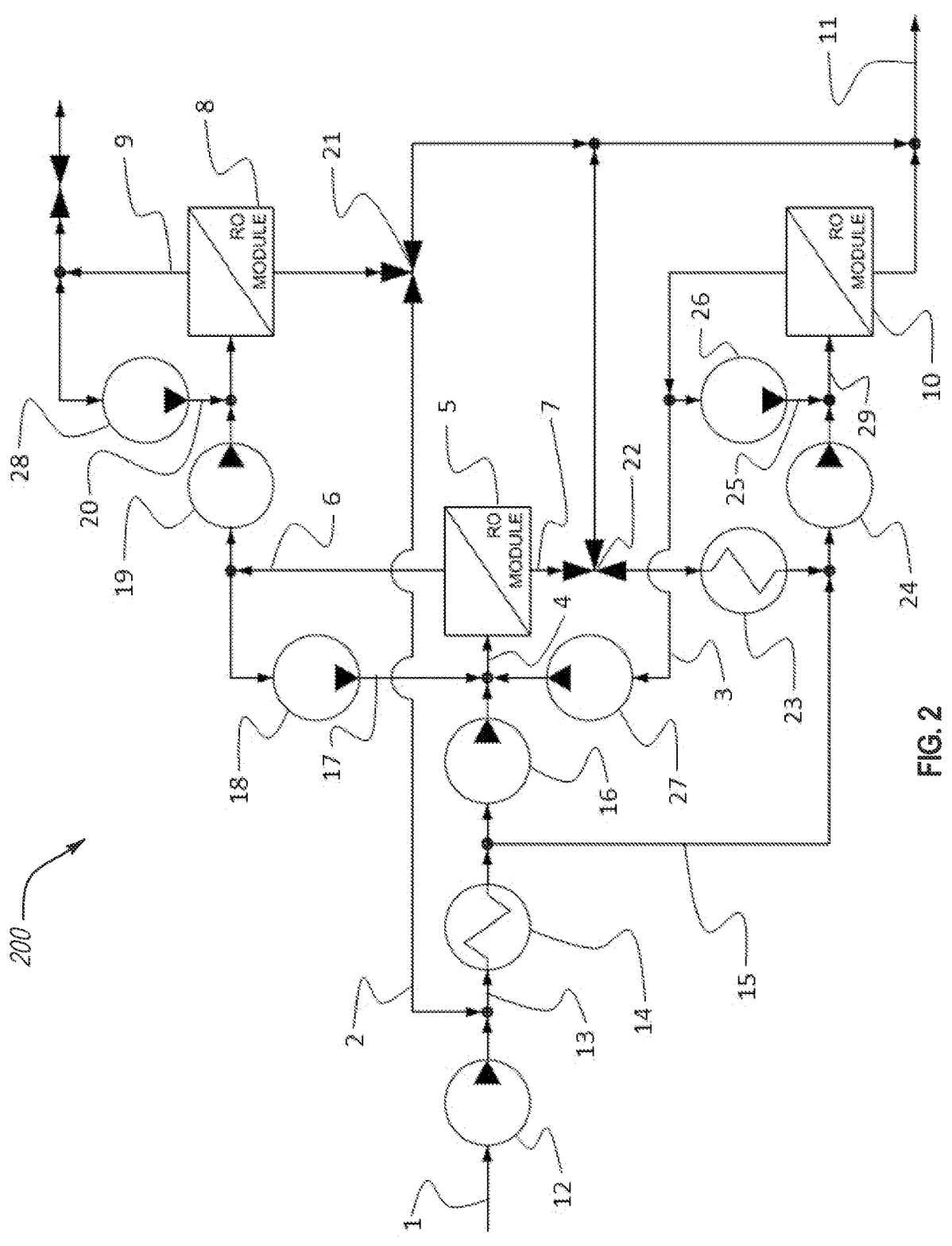
FIG. 2 is a schematic of a multi-tiered system for concentrating acetic acid solutions, according to at least some embodiments.

FIG. 2 is a schematic of a multi-tiered system 200 for concentrating acetic acid solutions, according to at least some embodiments. The system 200 may be similar or identical the system 100 in one or more aspects. The system 200 may be a specific implementation of the one or more components of the system 100. For example, the system 200 includes the first RO membrane module array 5, the second membrane module array 8, and the third membrane module array 10. The system 200 includes one or more pumps 12, 16, 27, 18, 25, 26, 19, or 28. The system 200 may include one or more heat exchangers 14 or 23. The system 200 includes plumbing (e.g., one or more conduits) and one or more valves to form recirculation loops for the membrane module arrays. The system 200 may include a recirculation loop added to each tier or stage to increase surface velocity on the UHP RO membrane elements (e.g., membranes) therein. In the system 200, the plumbing arrangements shown allow for clean-in-place (CIP) and hydrostatic pressure testing of the system.

The feed stream 1 may be pressurized by a low pressure centrifugal pump 12 to a low pressure (e.g., about 20-40 psi (137.9 kPa-275.8 kPa)). Feed stream 1 may be supplied by or constitute an acetic acid solution (e.g., vinegar) supply. Feed stream 1 may be combined with permeate stream 2 having a low pressure, forming a combined stream 13. The combined stream 13 may then be passed through a heat exchanger 14 where the temperature of the combined stream 13 is controlled to a set point between 2° C. and 30° C. Heat exchangers may include a liquid heat exchanger, a shell and tube heat exchanger, an open tube heat exchanger, or any other type of heat exchanger. In some examples, a heat exchanger may include a heat sink or chiller. A bypass feed supply 15 (e.g., valve and plumbing) to the third membrane module array 10 may be located downstream from the heat exchanger 14. The bypass feed supply 15 connects to the feed stream 1, and the flow through this bypass feed supply 15 may be zero or very close to zero during standard operation of a vinegar concentration process. The combined stream 13 may be pressurized to an ultrahigh pressure (e.g., 1200 psi (8.3 MPa) to 2000 psi (13.8 MPa), at least 1500 psi (10.3 MPa), or at least 1750 psi (12.1 MPa)) by a high pressure pump 16 plumbed to the first ultrahigh pressure reverse osmosis membrane module array 5. This high pressure stream output from the high pressure pump 16 may be combined with stream 3 and optionally combined with recirculated stream 17 to form combined stream 4. Combined stream 4 may be delivered to the first RO membrane module array 5 at the ultrahigh pressure. The first RO membrane module array 5 may operate at flux between 5 LMH and 50 LMH, for example 30 LMH.

Concentrate stream 6 is produced by the first RO membrane module array 5 as disclosed with respect to the system 100. The concentrate stream 6 may have a pressure below the pressure of the combined stream (e.g., a reduced pressure of 1710 psi (11.8 MPa)). A portion of the concentrate stream 6 (e.g., 20% to 90%) may be pressurized by a high pressure pump 18 (e.g., centrifugal pump) back to the pressure of the combined stream 4 (e.g., 1750 psi (12.1 MPa)) and recirculated back to the inlet of the first RO membrane module array 5, such as combined with stream 4. Such recirculation may be utilized to increase surface speed on the first RO membrane module array 5. Such increased surface speed may improve membrane performance, reduce fouling or scaling of the membrane, or allow the use of relatively larger diameter membranes, for example 8040 size membrane, in applications where low flow rates are less than 7 gallons per minute (GPM) for relatively clean water (e.g., water without solids) or less than 27 GPM for water with relatively high solids or foulants, to provide adequate surface speeds to prevent fowling or provide a selected level of performance.

Prior to the second RO membrane module array 8, concentrate stream 6 may be pressurized, such as back to the pressure of the combined stream 4 (e.g., the pressure of concentrate stream 6 or 1710 psi (11.8 MPa) to 1750 psi (12.1 MPa)) by a high pressure pump 19 (e.g., high pressure centrifugal or high pressure booster pump). Concentrate stream 6 may be combined with a recirculated stream 20 from the concentrate stream 9 of the second RO membrane module array. The combination of the recirculated stream 20 and the concentrate stream 6 may be fed to the second RO membrane module army 8. Concentrate stream 9 is produced by the second RO membrane module array 8 at a pressure below the pressure of the combined stream entering the second RO membrane module array 8 (e.g., a reduced pressure of 1710 psi (11.8 MPa)). A portion of the final or product concentrate stream 9 (e.g., 20% to 90%), may be pressurized by a high pressure pump 28 back to the pressure of the stream entering the second RO membrane module (e.g., 1750 psi (12.1 MPa)) and recirculated back to the inlet of the second RO membrane module array 8, such as after being combined with concentrate stream 6. The remainder of stream 9 may be delivered as the final product of the system 200. For example, the concentrate stream 9 may be routed to a product vessel or outlet. Permeate stream 2 is produced by the second RO membrane module army 8 at a low pressure (e.g., 20 psi to 40 psi (137.9 kPa-275.8 kPa)) and may be directed by divert valve 21 to be combined with stream 1, such as prior to the high pressure pump 16.

Referring back to the first RO membrane module army 5, permeate stream 7 may be produced at a low pressure (e.g., 20 psi to 40 psi (137.9 kPa-275.8 kPa)). Permeate stream 7 may be directed by divert valve 22 to a high pressure pump 24 where it is pressurized to an ultrahigh pressure, such as the pressure of combined stream 4 as it enters the first RO membrane module army 5. The permeate stream 7 may be routed through an optional heat exchanger 23 to control the temperature of the permeate stream 7 prior to the high pressure pump 24. This high pressure permeate stream 7 may be optionally combined with a recirculated stream 25 to form combined stream 29, and delivered to the third RO membrane module array 10. The third RO membrane module array 10 may operate at flux between 5 LMH and 50 LMH, for example 30 LMH. Concentrate stream 3 is produced by the third RO membrane module array 10 at a pressure below the pressure of the permeate stream 7 after high pressure pump 24 and the recirculation stream 25 entering the RO membrane module array 10 (e.g., 1710 psi (11.8 MPa)). A portion of the concentrate stream 3 (e.g., 20% to 90%) may be pressurized by a high pressure pump 26 back to the pressure of permeate stream 7 entering the third RO membrane module array 10 (e.g., 1750 psi (12.1 MPa)). Concentrate stream 3 may be recirculated back to the inlet of the third RO membrane module array 10 through the high pressure pump 26 and combined with permeate stream 7 exiting the high pressure pump 24. The remainder of concentrate stream 3 may be pressurized by a high pressure pump 27 (e.g., centrifugal pump) back to a pressure of the combined stream 4 (e.g., 1750 psi (12.1 MPa)). The pressurized remainder of the concentrate stream 3 may be recombined with feed stream 1 and other recirculated streams to form combined stream 4. The permeate stream 11 from the third RO membrane module array 10 may be produced at a low pressure (e.g., 0 psi to 40 psi (0 kPa-275.8 kPa)). The permeate stream 11 may leave the system 200 at a concentration below 2 wt % acetic acid (e.g., no more than 1 wt %).

The multi-tier or multi-stage concentration systems 100 and 200 are designed to leverage an acetic acid membrane rejection of 65-86%. Fundamentally, a significant portion of acetic acid is able to pass through the first stage and leave as permeate, feeding the third stage. Acetic acid is also hazardous, and spray leaks represent a significant danger to operators and adjacent equipment. For this reason, a safe solute should be used for pressure testing. Such a solute may be a simple salt (e.g., sodium chloride), a sugar, or alcohol sugar (e.g., glycerin). These safe solutes have a very high rejection with UHP RO membranes, such as greater than 98%. For this reason, it would be impossible to build pressure in the third stage, as there would not be a high enough concentration of solute, or a high enough osmotic pressure to build pressure in the third stage. This is also a consideration when cleaning the membrane(s) in the membrane module arrays as membrane cleaner(s) are well rejected by the UHP RO membranes. Thus, circulating membrane cleaner through the systems 100 or 200 starting at the first RO membrane module would be unable to reach the third RO stage. By adding a bypass feed supply 15, feed is able to reach the third membrane module array 10 directly to clean or test the third membrane module array 10. During a cleaning or testing mode, both divert valve 21 and divert valve 22 are diverting fluids flowing therethrough to combine with the permeate stream 11 which prevents dilution of the cleaning and testing solution. Additionally, the first high pressure pump 16 may be operated more slowly, or turned off entirely. The third high pressure pump 24 may be run at a higher flow rate than standard operating mode, allowing feed flow to bypass the first UHP reverse osmosis membrane module array 5 via the bypass 15.

While FIGS. 1 and 2 are schematics of three-tiered systems for concentrating acetic acid solutions, more tiers may be utilized. For example, for acetic acid solutions containing higher concentrations of acetic acid than about 20 wt %, it may be useful to utilize at least a fourth membrane module array. The permeate stream of the fourth membrane module array may be plumbed to the feed of the first UHP reverse osmosis membrane module array and the concentrate stream may be plumbed (e.g., fluidly connected) to the inlet of the second membrane module array. Such a configuration may be used to process relatively higher concentrations of acetic acid to provide a purer third permeate stream 11 and more concentrated second concentrate stream 9.

Portions of the system 100 or 200 may be constructed of a corrosion resistant material such as stainless steel, nylon, polytetrafluoroethylene, a zirconium coated metal, or the like. For example, the conduits connecting the various streams to the UHP RO module arrays. The pumps, heat exchangers, housing of the membrane modules, or other components in the systems may be constructed of one or more corrosion resistant materials.

The systems 100 and 200 may be used to process acetic acid solutions to provide acetic acid concentrate having relatively high concentration of acetic acid (e.g., at least 25 wt % acetic acid) and relatively pure water (e.g., less than 2 wt % acetic acid or less than 1 wt % acetic acid in water).

FIG. 3 is a flow diagram of a method 300 for concentrating acetic acid solutions, according to an embodiment. The method 300 includes block 310 of subjecting a feed stream including an acetic acid solution to a first ultrahigh pressure ("UHP") reverse osmosis process to form a first concentrate stream and a first permeate stream, a block 320 of subjecting the first concentrate stream to a second UHP reverse osmosis process to form a second concentrate stream and a second permeate stream, and a block 330 of subjecting the first permeate stream to a third UHP reverse osmosis process to form a third permeate stream and a third concentrate stream. In some embodiments, the method 300 may include more or fewer blocks than the blocks 310, 320, or 330. For example, some of the blocks 310, 320, or 330 may be combined into a single block. Additional blocks may be added in some embodiments. The method 300 may be implemented utilizing any of the systems disclosed herein or according to any of the flow diagrams of the systems disclosed herein.

The block 310 of subjecting a feed stream including an acetic acid solution to a first UHP reverse osmosis process to form a first concentrate stream and a first permeate stream may include circulating the feed stream through a first UHP reverse osmosis membrane module array at an ultrahigh pressure. For example, subjecting a feed stream including an acetic acid solution to a first UHP reverse osmosis process may include feeding the feed stream into the first UHP reverse osmosis module array at a pressure of at least 1200 psi (8.3 MPa), such as 1200 psi (8.3 MPa) to 2000 psi (13.8 MPa), 1200 psi (8.3 MPa) to 1500 psi (10.3 MPa), 1500 psi (10.3 MPa) to 2000 psi (13.8 MPa), at least 1500 psi (10.3 MPa), or at least 1750 psi (12.1 MPa). Subjecting the feed stream to the first UHP reverse osmosis process may include circulating a feed stream including the acetic acid solution through a first UHP reverse osmosis membrane module array at a first ultrahigh pressure (e.g., at least 1200 psi (8.3 MPa), at least 1500 psi (10.3 MPa), or at least 1750 psi (12.1 MPa)) to form the first concentrate stream and the first permeate stream.

The first UHP reverse osmosis module array may include one or more UHP reverse osmosis modules. The one or more UHP reverse osmosis membrane modules may include any of the (UHP) reverse osmosis modules disclosed herein. The one or more UHP reverse osmosis membrane modules may be arranged in parallel or in series.

The feed stream may include at least 5 wt % acetic acid, such as 5 wt % to 30 wt % acetic acid, 5 wt % to 20 wt % acetic acid, 15 wt % to 30 wt % acetic acid, 7 wt % to 17 wt % acetic acid, at least 7 wt % acetic acid, or at least 10 wt % acetic acid. The feed stream or acetic acid solution may include vinegar, such as a distilled or a filtered vinegar that includes mainly water and acetic acid and does not include significant amounts of dissolved or suspended solids that may be present in other types of vinegars, such as balsamic vinegar.

At least a portion of the feed stream may be recirculated through the first UHP reverse osmosis membrane module array 5, such as to selectively control the flow rate of the combined feed stream 4. For example, at least a portion of the first permeate 7 or the first concentrate stream 6 may be recirculated back to form a portion of the combined feed stream 4. Recirculation of at least a portion of the feed may be preferred if the selected flow rates are not met by the incoming feed flow (e.g., flow rate of feed stream 1). Flow rates for an 8040 UHP reverse osmosis element (e.g., membrane) may be at least 7 GPM for feed water at post RO quality and 27 GPM for feed water that is a lesser quality compared to post RO water.

The block 320 of subjecting the first concentrate stream to a second UHP reverse osmosis process to form a second concentrate stream and a second (reverse osmosis) permeate stream may include circulating the first concentrate stream through a second UHP reverse osmosis membrane module array at an ultrahigh pressure. For example, subjecting the first concentrate stream to a second UHP reverse osmosis process may include feeding the first concentrate stream into the second UHP reverse osmosis module array at a pressure of at least 1200 psi (8.3 MPa), such as 1200 psi (8.3 MPa) to 2000 psi (13.8 MPa), 1200 psi (8.3 MPa) to 1500 psi (10.3 MPa), 1500 psi (10.3 MPa) to 2000 psi (13.8 MPa), at least 1500 psi (10.3 MPa), or at least 1750 psi (12.1 MPa). Subjecting the first concentrate stream to the second UHP reverse osmosis process may circulating the first concentrate stream through a second UHP reverse osmosis membrane module array at a second ultrahigh pressure (e.g., at least 1200 psi (8.3 MPa), at least 1500 psi (10.3 MPa), or at least 1750 psi (12.1 MPa)) to form a second concentrate stream and a second permeate stream.

The second UHP reverse osmosis module array may include one or more UHP reverse osmosis modules. The one or more UHP reverse osmosis membrane modules may include any of the (UHP) reverse osmosis modules disclosed herein. The one or more UHP reverse osmosis membrane modules may be arranged in parallel or in series.

The second concentrate stream includes at least 25 wt % acetic acid, such as at least 30 wt % acetic acid. Water may be the majority of the remainder of the second concentrate stream. The second concentrate stream may be a product, which may be directed to a collection vessel (e.g., stainless steel tank, zirconium coated tank, polymer tank, or the like) for transport or storage. For example, the method 300 may include outputting the second concentrate stream to a storage vessel.

The second permeate stream may include acetic acid and water. The second permeate stream may have a lower concentration of acetic acid than the feed stream. The second permeate stream may be recycled, such as combined with the feed stream prior to the first UHP reverse osmosis membrane module array. For example, the method 300 may include recirculating at least a portion of the second permeate stream to be used as at least a portion of a combined feed stream in the first ultrahigh pressure reverse osmosis process.

The block 330 of subjecting the first permeate stream to a third UHP reverse osmosis process to form a third permeate stream and a third (reverse osmosis) concentrate stream may include circulating the first permeate stream through a third UHP reverse osmosis membrane module array at an ultrahigh pressure. For example, subjecting the first permeate stream to a third UHP reverse osmosis process may include feeding the first permeate stream into the third UHP reverse osmosis module array at a pressure of at least 1200 psi (8.3 MPa), such as 1200 psi (8.3 MPa) to 2000 psi (13.8 MPa), 1200 psi (8.3 MPa) to 1500 psi (10.3 MPa), 1500 psi (10.3 MPa) to 2000 psi (13.8 MPa), at least 1500 psi (10.3 MPa), or at least 1750 psi (12.1 MPa). Subjecting the first permeate stream to the third UHP reverse osmosis process may include circulating the first permeate stream through a third UHP reverse osmosis membrane module array at a third ultrahigh pressure (e.g., at least 1200 psi (8.3 MPa), at least 1500 psi (10.3 MPa), or at least 1750 psi (12.1 MPa)) to form a third concentrate stream and a third permeate stream.

The third UHP reverse osmosis module array may include one or more UHP reverse osmosis modules. The one or more UHP reverse osmosis membrane modules may include any of the (UHP) reverse osmosis modules disclosed herein. The one or more UHP reverse osmosis membrane modules may be arranged in parallel or in series.

The third permeate stream includes 2 wt % or less acetic acid, such as 1 wt % or less acetic acid. Third permeate may be substantially pure water or water that is at least suitable for disposal in a municipal waste water system (some wastewater systems cannot be utilized when the acetic acid concentration is above 2 wt % or above 3 wt %). The third permeate stream may be a product, which may be directed to a collection vessel or supply for transport or storage. For example, the method 300 may include outputting the third permeate stream to a wastewater outlet.

The third concentrate stream may include acetic acid and water. The third concentrate stream may have a lower concentration of acetic acid than the feed stream. The third concentrate stream may be recycled, such as combined with the feed stream prior to the first UHP reverse osmosis membrane module array. For example, the method 300 may include recirculating at least a portion of the third concentrate stream to be used as at least a portion of a combined feed stream in the first ultrahigh pressure reverse osmosis process. The method 300 may include combining the feed stream, the second permeate stream, and the third concentrate stream, such as to form a combined feed stream, prior to subjecting the feed stream to the first ultrahigh reverse osmosis process.

The pressures of the first UHP reverse osmosis process, the second UHP reverse osmosis process, and the third UHP reverse osmosis process may be the same or may differ therebetween. For example, the first UHP reverse osmosis process may be carried out at a higher pressure than the second or third UHP reverse osmosis processes. Accordingly, the method 300 may include controlling the pressure of the various streams to selected ultrahigh pressures, such as through one or more pumps. The pressure(s) may be selected based on the acetic acid content of the feed stream, the UHP membrane type, the flow rate through the UHP reverse osmosis membrane module arrays, the temperature of the various streams in the system, or the like.

The method may further include controlling the temperature of one or more of the feed stream, the first concentrate stream, the first permeate stream, the second concentrate stream, the second concentrate stream, the third concentrate stream, or the third permeate stream. Controlling the temperature may include circulating the respective stream(s) through one or more heat exchangers. The temperature of the respective streams may be controlled to a temperature of between 2° C. and 30° C., such as between 5° C. and 20° C., 5° C. and 20° C., 7° C. and 17° C., less than 25° C., or less than 20° C.

While FIGS. 1 and 2 are schematics of three-tiered systems for concentrating acetic acid solutions, FIGS. 1 and 2 also represent flow charts for methods of concentrating acetic acid solutions, such as described with respect to FIG. 3. Specific examples of methods of concentrating acetic acid solutions are disclosed in more detail below.

PROPHETIC EXAMPLES

Example 1: Feed at 15 wt % Acetic Acid
Producing Concentrate at 30.1 wt %

With reference to FIG. 1, a feed stream 1 composed of 15.0 wt % acetic acid (vinegar) is introduced into the system at a mass flow rate of 100 kg per minute. The feed stream 1 is combined with two other streams, second permeate stream 2 composed of 8.1 wt % acetic acid at a mass flow rate of 33 kg per minute, and third concentrate stream 3 composed of 8.6 wt % acetic acid at a mass flow rate of 33 kg per minute, forming combined (feed) stream 4 composed of 12.3 wt % acetic acid at a mass flow rate of 167 kg per minute. Combined stream 4 may be temperature controlled at this point, for example by a heat exchanger, to a temperature of between 5° C. and 20° C., for example 15° C. Combined stream 4 is then pressurized to an ultrahigh pressure, between 1200 psi (8.3 MPa) and 2000 psi (13.8 MPa), for example 1750 psi (12.1 MPa), and delivered to the first UHP reverse osmosis membrane module array 5, which may operate at flux between 5 LMH and 50 LMH, for example 24 LMH.

The first UHP reverse osmosis membrane module array 5 may operate between 30% and 75% recovery by mass, for example 51% recovery by mass, rejecting 76% of the acetic acid, producing the first concentrate stream 6 composed of 21.1 wt % acetic acid at a mass flow rate of 82 kg per minute, and the first permeate stream 7 composed of 3.9 wt % acetic acid at a mass flow rate of 85 kg per minute.

The first concentrate stream 6 may be temperature controlled at this point, for example by a heat exchanger, to a temperature of between 5° C. and 20° C. (e.g., 15° C.). The first concentrate stream 6 is then (re)pressurized to an ultrahigh pressure, between 1200 psi (8.3 MPa) and 2000 psi (13.8 MPa), for example 1750 psi (12.1 MPa), and delivered to the second UHP reverse osmosis membrane module array 8, which may operate at flux between 5 LMH and 50 LMH, for example 16 LMH. The second UHP reverse osmosis membrane module array 8 may operate between 30% and 75% recovery by mass, for example 41% recovery by mass, rejecting 68% of the acetic acid, producing second concentrate stream 9 composed of 30.1 wt % acetic acid at a mass flow rate of 48 kg per minute, and second permeate stream 2 which is recycled back to the first UHP reverse osmosis membrane module array 5. The second concentrate stream 9 is now at a final concentration, and leaves the system to be collected.

The first permeate stream 7 may be temperature controlled at this point, for example by a heat exchanger, to a temperature of between 5° C. and 20° C. (e.g., 15° C.). The first permeate stream 7 is then (re)pressurized to an ultrahigh pressure, between 1200 psi (8.3 MPa) and 2000 psi (13.8 MPa), for example 1750 psi (12.1 MPa), and delivered to the third UHP reverse osmosis membrane module array 10, which may operate at flux between 5 LMH and 50 LMH, for example 32 LMH. The third UHP reverse osmosis membrane module array 10 may operate between 30% and 75% recovery by mass, for example 61% recovery by mass, rejecting 84% of the acetic acid, producing third concentrate stream 3 and third permeate stream 11 composed of 1.0 wt % acetic acid at a mass flow rate of 52 kg per minute. The third permeate stream 11 is now at a sufficiently low concentration to be discharged to waste water treatment or recycled back into an upstream process.

Example 2: Feed of 8 wt % Acetic Acid Producing Concentrate at 29.9 wt %

With reference to FIG. 1, a feed stream 1 composed of 8.0 wt % acetic acid (vinegar) is introduced into the system at a mass flow rate of 100 kg per minute. It is combined with two other streams, second permeate stream 2 composed of 5.7 wt % acetic acid at a mass flow rate of 43 kg per minute, and third concentrate stream 3 composed of 4.5 wt % acetic acid at a mass flow rate of 44 kg per minute, forming a combined (feed) stream 4 composed of 6.7 wt % acetic acid at a mass flow rate of 187 kg per minute. Combined stream 4 may be temperature controlled at this point, for example by a heat exchanger, to a temperature of between 5° C. and 20° C. (e.g., 15° C.). Combined stream 4 is then pressurized to an ultrahigh pressure, between 1200 psi (8.3 MPa) and 2000 psi (13.8 MPa), for example 1750 psi (12.1 MPa), and delivered to the first UHP reverse osmosis membrane module array 5, which may operate at flux between 5 LMH and 50 LMH, for example 30 LMH.

The first UHP reverse osmosis membrane module array 5 may operate between 30% and 75% recovery by mass, for example 63% recovery by mass, rejecting 82% of the acetic acid, producing first concentrate stream 6 composed of 14.7 wt % acetic acid at a mass flow rate of 69 kg per minute, and first permeate stream 7 composed of 2.0 wt % acetic acid at a mass flow rate of 118 kg per minute.

First concentrate stream 6 may be temperature controlled at this point, for example by a heat exchanger, to a temperature of between 2° C. and 30° C. (e.g., 15° C.). First concentrate stream 6 is then pressurized to an ultrahigh pressure, between 1200 psi (8.3 MPa) and 2000 psi (13.8 MPa), for example 1750 psi (12.1 MPa), and delivered to the second UHP reverse osmosis membrane module array 8, which may operate at flux between 5 LMH and 50 LMH, for example 22 LMH. The second UHP reverse osmosis membrane module array 8 may operate between 30% and 75% recovery by mass, for example 63% recovery by mass, rejecting 74% of the acetic acid, producing the second concentrate stream 9 composed of 29.9 wt % acetic acid at a mass flow rate of 26 kg per minute, and the second permeate stream 2 which is recycled back to the first UHP reverse osmosis membrane module array 5. The second concentrate stream 9 is now at a final concentration, and leaves the system to be collected.

The first permeate stream 7 may be temperature controlled at this point, for example by a heat exchanger, to a temperature of between 2° C. and 30° C. (e.g., 15° C.). First permeate stream 7 is then pressurized to an ultrahigh pressure, between 1200 psi (8.3 MPa) and 2000 psi (13.8 MPa), for example 1750 psi (12.1 MPa), and delivered to the third UHP reverse osmosis membrane module array 10, which may operate at flux between 5 LMH and 50 LMH, for example 34 LMH. The third UHP reverse osmosis membrane module array 10 may operate between 30% and 75% recovery by mass, for example 63% recovery by mass, rejecting 86% of the acetic acid, producing third concentrate stream 3 and third permeate stream 11 composed of 0.5 wt % acetic acid at a mass flow rate of 74 kg per minute. The third permeate stream 11 is now at a sufficiently low concentration to be discharged to waste water treatment or recycled back into an upstream process.

The multi-tier methods and systems for concentrating acetic acid solutions disclosed herein are not possible with typical reverse osmosis ("RO") membrane modules operating at "high pressure" between 500 psi (3.4 MPa) and 1200 psi (8.3 MPa). For example, they are not possible in three tiers. Rather, to reach a concentration of 30 wt/o acetic acid, the "high pressure" approach would require six recirculation tiers due to the relatively low rejection of acetic acid operating at these pressures in reverse osmosis modules. This number of stages results in systems that were not commercially viable to reach 30 wt % acetic acid, both in capital and operational expenditure.

The systems and methods disclosed herein allow acetic acid solutions to be processed at two times the flux and two times the rejection of a high pressure system. The ultrahigh pressure multi-tier osmosis systems and methods disclosed herein capable of concentrating acetic acid to 30 wt % in only three tiers, a process that is commercially viable in capital and operational expenditure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for concentrating acetic acid solutions, the method comprising:

subjecting a feed stream including an acetic acid solution to a first ultrahigh pressure reverse osmosis process to form a first concentrate stream and a first permeate stream;

subjecting the first concentrate stream to a second ultrahigh pressure reverse osmosis process to form a second concentrate stream and a second permeate stream;

subjecting the first permeate stream to a third ultrahigh pressure reverse osmosis process to form a third permeate stream and a third concentrate stream; and combining the feed stream, the second permeate stream, and the third concentrate stream prior to subjecting the feed stream to the first ultrahigh reverse osmosis process.

2. The method of claim 1 wherein the feed stream includes 7 weight percent (wt %) to 17 wt % acetic acid and the second concentrate stream includes at least 25 wt % acetic acid.

3. The method of claim 1 wherein the second concentrate stream includes at least 30 wt % acetic acid.

4. The method of claim 1 wherein the third permeate stream includes 2 wt % acetic acid or less.

5. The method of claim 1 wherein the acetic acid solution includes vinegar.

6. The method of claim 1 wherein subjecting a feed stream including an acetic acid solution to a first ultrahigh pressure reverse osmosis process includes circulating the feed stream through a first ultrahigh pressure membrane module array at an ultrahigh pressure.

7. The method of claim 1 wherein the ultrahigh pressure is at least 1750 psi.

8. The method of claim 1 further comprising recirculating at least a portion of one or more of the second permeate stream or the third concentrate stream to form at least a portion of a combined feed stream in the first ultrahigh pressure reverse osmosis process.

9. A method for concentrating acetic acid solutions, the method comprising:

subjecting a feed stream including an acetic acid solution to a first ultrahigh pressure reverse osmosis process to form a first concentrate stream and a first permeate stream;

subjecting the first concentrate stream to a second ultrahigh pressure reverse osmosis process to form a second concentrate stream and a second permeate stream; and subjecting the first permeate stream to a third ultrahigh pressure reverse osmosis process to form a third permeate stream and a third concentrate stream, wherein subjecting a feed stream including an acetic acid solution to a first ultrahigh pressure reverse osmosis process includes circulating the feed stream through a first ultrahigh pressure membrane module array at an ultrahigh pressure, wherein subjecting the first concentrate stream to a second ultrahigh pressure reverse osmosis process to form a second concentrate stream and a second permeate stream includes circulating the first concentrate stream through a second ultrahigh pressure membrane module array at the ultrahigh pressure.

10. The method of claim 9 wherein subjecting the first permeate stream to a third ultrahigh pressure reverse osmosis process to form a third permeate stream and a third concentrate stream includes circulating the first permeate stream through a second ultrahigh pressure membrane module array at the ultrahigh pressure.

11. A system for concentrating acetic acid solutions, the system comprising:

a first ultrahigh pressure reverse osmosis membrane module array configured to receive a feed stream including an acetic acid solution and produce a first concentrate stream and a first permeate stream;

a second ultrahigh pressure reverse osmosis membrane module array configured to receive the first concentrate stream and produce a second concentrate stream and a second permeate stream; and a third ultrahigh pressure reverse osmosis membrane module array configured to receive the first permeate stream and produce a third concentrate stream and a third permeate stream, wherein the second permeate stream is fluidly connected to the third concentrate stream and the feed stream prior to the first ultrahigh pressure reverse osmosis membrane module array.

12. The system of claim 11 wherein the first ultrahigh pressure reverse osmosis membrane module array, the second ultrahigh pressure reverse osmosis membrane module array, and the third ultrahigh pressure reverse osmosis membrane module array includes one or more ultrahigh pressure reverse osmosis membrane modules having reverse osmosis membranes configured to operate at a pressure of 1200 psi or higher.

13. The system of claim 12 wherein the reverse osmosis membranes are configured to operate at a pressure of 1750 psi or higher.

14. The system of claim 11 wherein one or more of the first ultrahigh pressure reverse osmosis membrane module array, the second ultrahigh pressure reverse osmosis membrane module array, or the third ultrahigh pressure reverse osmosis membrane module array includes a plurality of ultrahigh pressure reverse osmosis membrane modules.

15. The system of claim 11 further comprising an acetic acid solution supply fluidly connected to the to the first reverse osmosis membrane module array via the feed stream.

16. The system of claim 15 wherein the acetic acid solution includes vinegar.

17. A method for concentrating acetic acid solutions, the method comprising:

circulating a feed stream including an acetic acid solution through a first ultrahigh pressure reverse osmosis membrane module array at a first pressure of at least 1500 psi to form a first concentrate stream and a first permeate stream;

circulating the first concentrate stream through a second ultrahigh pressure reverse osmosis membrane module array at a second pressure of at least 1500 psi to form a second concentrate stream and a second reverse osmosis permeate;

circulating the first permeate stream through a third ultrahigh pressure reverse osmosis membrane module array at a third pressure of at least 1500 psi to form a third permeate stream and a third reverse osmosis concentrate; and combining the feed stream, the second reverse osmosis permeate, and the third reverse osmosis concentrate prior to circulating the feed stream through the first ultrahigh pressure reverse osmosis membrane module array.

18. The method of claim 17, wherein one or more of the first pressure, the second pressure, or the third pressure are at least 1750 psi.

* * * * *